United States Patent [19]
Gunawardana et al.

[11] Patent Number: 5,530,020
[45] Date of Patent: Jun. 25, 1996

[54] TAXOL DERIVATIVES

[75] Inventors: Geewananda P. Gunawardana, Libertyville; Larry L. Klein, Lake Forest; James B. McAlpine, Libertyville, all of Ill.

[73] Assignee: Abbott Laboratories, Abbott Park, Ill.

[21] Appl. No.: 317,978

[22] Filed: Oct. 4, 1994

Related U.S. Application Data

[60] Division of Ser. No. 46,678, Apr. 14, 1993, Pat. No. 5,352,806, which is a continuation-in-part of Ser. No. 914,720, Jul. 16, 1992, abandoned, which is a continuation-in-part of Ser. No. 870,509, Apr. 17, 1992, abandoned.

[51] Int. Cl.$^6$ ...................... C07D 305/14; A61K 31/335
[52] U.S. Cl. ........................................... 514/449; 549/510
[58] Field of Search ............................ 549/510; 514/449

[56] References Cited

U.S. PATENT DOCUMENTS 5,367,086  11/1994  Rao ........................................ 549/510

OTHER PUBLICATIONS

Pulicani et al., Tet. Lett. (1994), 35(28), 4999–5002.

*Primary Examiner*—Johann Richter
*Assistant Examiner*—John Peabody
*Attorney, Agent, or Firm*—Thomas D. Brainard; Andreas M. Danckers

[57] ABSTRACT

Compounds having the formula

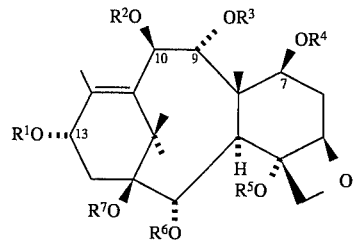

wherein —$OR^1$ comprises the C-13 side-chain of taxol and $R^3$ comprises hydrogen, as well as a method for the preparation thereof.

5 Claims, 2 Drawing Sheets

TAXOL DERIVATIVES

This application is a Divisional of application Ser. No. 08/046,678, file Apr. 14, 1993, now U.S. Pat. No. 5,352,806, which is a continuation-in-part of copending U.S. patent application Ser. No. 07/914,720, filed Jul. 16, 1992 now abandoned which is a continuation-in-part of U.S. patent application Ser. No. 07/870,509, filed Apr. 17, 1992, now abandoned.

BACKGROUND OF THE INVENTION

The present invention relates to plant-derived chemotherapeutic compounds. More particularly, the invention is directed to 9-dihydro-13-acetylbaccatin III, a natural product isolated from *Taxus canadenis*, as well as novel analogs of taxol prepared therefrom.

Taxol, a member of the taxane family of terpenes, is of interest as a chemotherapeutic agent against a broad range of cancers. Taxol has been shown to be effective against advanced breast and ovarian cancers in clinical trials, and has exhibited promising activity against a number of other tumor types in preliminary investigations. A summary of the current state of taxol research, development and clinical testing may be found in Borman, *Chemical & Engineering News* (Sept. 2, 1991), 11–18; a review of synthetic efforts in the taxol field is provided by D. G. I. Kingston in *Pharmacol. Therap.* (1992), in press.

Taxol, which possesses the structural formula is currently limited in supply, as it is obtained by extraction primarily from the bark and, to a lesser amount, the leaves of trees and bushes of the genus Taxus. The primary source of taxol, the Pacific yew *Taxus brevifolia*, is a slow-growing evergreen with limited geographic distribution and increasing scarcity. Furthermore, the isolation of taxol, which constitutes less than 400 parts per million of the tree bark, is a difficult, low-yield and expensive process. Neither long-term nor large-scale harvesting of yews is considered an acceptable option for ecological as well as commercial reasons. There is, consequently, a pressing need for additional supplies of taxol for clinical use and testing.

While the needles of other Taxus species are being explored as renewable sources of taxol and its precursors, other researchers have attempted to produce taxol in tissue and cell culture. Total chemical synthesis of the compound and its related analogs has been attempted but not yet been achieved. The chemical conversion of naturally occurring taxol precursors such as baccatin III and cephalomannine to taxol itself or its analogs has been reported; however, additional routes for production of potentially active taxols and related compounds are still needed.

Taxol prodrugs or derivatives having greater water solubility than the naturally-occurring taxols have also been sought. In the search for new derivatives with potentially enhanced solubility, one of the sites on the molecule where attention has been directed is the ketone function at the C-9 position. Taxol is very resistant to reduction, and the C-9 carbonyl group is specifically resistant to reduction, even with various hydride reagents. Few compounds having anything other than a carbonyl group at C-9 have been disclosed. In U.S. Pat. No. 5,015,744 and U.S. Pat. No. 4,976,399, issued to Holton et al., taxol derivatives acetylated at the C-7, C-9 and C-10 positions are generically disclosed. The '744 patent does not, however, provide means for preparing the C-9 alkanoyloxy derivatives. The '399 patent contains illustrations of 7-deoxy compounds possessing both C-9 and C-10 O-acetyl groups. These compounds are taxol analogs that presumably may be synthesized via a taxusin synthesis, in which the vicinal hydroxyl groups are protected during the synthetic procedure with an acetonide group. There is no suggestion, however, that the free C-7, C-9 diol could be produced. Further, no scheme is proposed that would allow synthesis of analogs of taxol that possess a free hydroxyl group at C-9. Thus, the 9-dihydro derivatives of taxol and baccatin III have not been obtained as synthetic products, and 9-dihydro compounds in the taxol and baccatin series have not previously been isolated from natural sources.

The ability to synthesize 9-dihydrotaxol compounds having potentially superior pharmacologic properties may offer significant advantages to the chemist and pharmacologist. It is expected that a 9-dihydro derivative would have improved water solubility. Further, the 9-hydroxyl group of such a derivative would provide an additional functionality for further derivatization or prodrug preparation. In addition, the presence of a hydroxyl group instead of a carbonyl function at this position would impart greater stability to the molecule in that epimerization at position C-7, which has been shown to reduce the activity of the compound, would no longer be facile.

SUMMARY OF THE INVENTION

In one aspect of the present invention is disclosed the compound 9-dihydro-13-acetylbaccatin III, having the following structural formula (I):

a previously unknown constituent of the Canada yew, *Taxus canadensis*. In formula (I), "Ph" and "Ac" represent acetyl and phenyl radicals, respectively.

In another aspect of the invention are disclosed 9-dihydrotaxol analogs in general having in common with 9-dihydro-13-acetylbaccatin III the following structural formula (II):

(II)

as well as a process for preparing such compounds from 9-dihydro-13-acetylbaccatin III. $R^1$ in formula (II) is a group having the formula in which $R^8$ is hydrogen, alkyl, phenyl, substituted phenyl, alkoxy, substituted alkoxy, amino, substituted amino, phenoxy or substituted phenoxy; $R^9$ is hydrogen, alkyl, hydroxyalkyl, alkoxyalkyl, aminoalkyl, phenyl or substituted phenyl; and $R^{10}$ is hydrogen, alkanoyl, substituted alkanoyl or aminoalkanoyl.

$R^2$, $R^4$, $R^5$ and $R^7$ in formula (II) are independently hydrogen, alkyl, alkanoyl or aminoalkanoyl.

$R^3$ in formula (II) is hydrogen, alkyl or aminoalkanoyl.

$R^6$ in formula (II) is hydrogen, alkyl, alkanoyl, aminoalkanoyl or phenylcarbonyl (—C(O)-phenyl).

Alternatively, $R^3$ in formula (II), taken together with either $R^2$ or $R^4$, may form a ring having the formula wherein $R^{11}$ and $R^{12}$ are independently hydrogen, alkyl, phenyl or substituted phenyl; or, taken together, $R^{11}$ and $R^{12}$ are a single atom selected from the group consisting of oxygen and sulfur; or one of $R^{11}$ and $R^{12}$ is hydrogen, alkyl, phenyl or substituted phenyl, and the other is —$OR^{13}$ or —$NR^{13}R^{14}$ where $R^{13}$ and $R^{14}$ are independently alkyl, alkanoyl, substituted alkanoyl, phenyl or substituted phenyl.

It is expected that these compounds will be useful in connection with the treatment, or in the preparation of taxol derivatives for use in treatment, of cancers and leukemias.

BRIEF DESCRIPTION OF THE DRAWINGS

The present invention is disclosed in connection with the appended drawings, in which.

DETAILED DESCRIPTION OF THE INVENTION

The present invention comprises the compound 9-dihydro-13-acetylbaccatin III as well as derivatives thereof, including 9-dihydrotaxol, having the structural formula (II) wherein groups $R^1$ through $R^{12}$ are as described above. Included among the compounds of the invention are those wherein —$OR^1$ is the side-chain of taxol, a group having the formula Also included are those compounds in which $R^3$ is hydrogen, that is, the 9-dihydro analogs of taxol.

The following definitions apply to these compounds and throughout the present disclosure:

The term "alkyl" as used herein refers to a monovalent group derived by the removal of a single hydrogen atom from a straight- or branched-chain saturated hydrocarbon containing one to six carbon atoms including, but not limited to, methyl, ethyl, n- and/so-propyl, n-, sec-,/so- and tert-butyl, pentyl and hexyl.

The term "alkanoyl" as used herein refers to an alkyl function as defined above attached via a carbonyl group including, but not limited to, acetyl, propionyl, butanoyl and isobutanoyl.

The term "alkoxy" as used herein refers to an alkyl function as defined above attached via an oxygen atom including, but not limited to, methoxy, ethoxy, isopropoxy, butoxy and tert-butoxy.

The term "aminoalkanoyl" as used herein refers to an alkanoyl function as defined above substituted with between one and three amino groups including, but not limited to, 2-aminopropanoyl, 4-aminobutanoyl and 6-aminohexanoyl. Additionally, the amino groups may optionally be substituted with peptidyl residues of the naturally occurring amino acids, as well as di- and tripeptide residues formed therefrom.

The term "aminoalkyl" as used herein refers to an alkyl function as defined above substituted with amino or substituted amino, as defined elsewhere herein.

The term "halogen" as used herein refers to a group selected from bromo (Br), chloro (Cl), fluoro (F) and iodo (I).

The term "haloalkyl" as used herein refers to an alkyl group as defined above substituted with between one and three halogen atoms including, but not limited to, fluoromethyl, trifluoromethyl and fluoroethyl.

The terms "N-protected" and "N-protecting" as used herein refer to the use of a group intended to protect an amino function or the N-terminus of an amino acid or peptide against undesirable reactions during a synthetic procedure or to prevent the attack of exopeptidases on the compound or to increase the solubility of the compound and includes, but is not limited to, such uses of sulfonyl; acyl, such as acetyl, pivaloyl and benzoyl; alkoxycarbonyl, such as tert-butyloxycarbonyl (BOC), benzyloxycarbonyl (Cbz); and L- or D-aminoacyl residues, which may themselves be N-protected. Other examples may be found in *The Peptides*, E. Gross and J. Meienhofer, Vol. 3, Academic Press (1981), incorporated herein by reference.

The term "prodrug" as used herein refers to compounds that are rapidly transformed in vivo to yield the parent compounds of Formula (I), as for example by hydrolysis in blood. T. Higuchi and V. Stella provide a thorough discussion of the prodrug concept in "Prodrugs as Novel Delivery Systems", A.C.S. Symposium Series, Vol. 14, American Chemical Society (1975), incorporated herein by reference. Examples of esters useful as prodrugs for compounds containing carboxyl groups can be found on pages 14–21 of "Bioreversible Carriers in Drug Design: Theory and Application", ed. E. B. Roche, Pergamon Press (1987), incorporated herein by reference.

The term "prodrug ester group" as used herein refers to any of several ester-forming groups that are hydrolyzed under physiological conditions. Examples of prodrug ester groups include pivaloyloxymethyl, acetoxymethyl, phthalidyl, indanyl and methoxymethyl, as well as other such groups known in the art.

The term "protecting group" as used herein is a term well-known in the art and refers to substituents on functional groups of compounds undergoing chemical transformation which prevent undesired reactions and degradations during a synthesis; see, for example, T. H. Greene, "Protective Groups in Organic Synthesis," John Wiley & Sons (1981), incorporated herein by reference.

The term "substituted alkanoyl" as used herein refers to an alkanoyl group as defined above substituted with between one and three groups such as hydroxyl, sulfhydryl, alkoxyl, carboxyl and halogen.

The term "substituted alkoxy" as used herein refers to an alkoxy group as defined above substituted with between one and three groups such as hydroxyl, sulfhydryl, alkoxyl, thioalkoxyl, carboxyl, amino and halogen.

The term "substituted amino" as used herein refers to an amino group substituted with one or two alkyl groups including, but not limited to, t-butylamino, benzylamino, and N,N-dimethylamino.

The term "substituted phenyl" as used herein refers to a phenyl group substituted with between one and three substituents independently selected from alkyl, halogen, haloalkyl, alkoxy, benzyloxy, thioalkoxy, hydroxy, alkanoyl, carboxy, amino, alkylamino, dialkylamino, nitro and —$OSO_3H$.

The term "substituted phenoxy" as used herein refers to a phenoxy group substituted with between one and three substituents independently selected from alkyl, halogen, haloalkyl, alkoxy, benzyloxy, thioalkoxy, hydroxy, alkanoyl, carboxy, amino, alkylamino, dialkylamino, nitro and —$OSO_3H$.

The term "thioalkoxy" as used herein refers to an alkoxy group as defined above wherein a sulfur atom is substituted for the oxygen atom.

The present invention also embraces a process for the preparation of the above compounds of formula (II) from the compound of formula (I), 9-dihydro-13-acetylbaccatin III (compound 1). This process comprises the steps of:

(a) protection of the C-7 and C-9 hydroxy groups of compound 1 via involvement in acetal formation;

(b) general deesterification (deacetylation) of the protected intermediate;

(c) addition of a suitable side-chain to the C-13 position; and (d) selective deprotection to provide the desired product.

It has been found that compound 1 of the present invention may be obtained by alcoholic extraction from crushed needles and twigs of *Taxus canadensis*. This extract is then purified using customary separatory techniques, beginning with partitioning between solvent systems consisting of acetone, methanol, hexane, heptane and water to remove fats and lipids. The defatted crude extract is further partitioned, in several stages, between solvent systems consisting of methanol, methylene chloride, chloroform, ethyl acetate and water. Those fractions of the extract which are soluble in a solvent system consisting either of methylene chloride or of chloroform and ethyl acetate contain compound 1.

The above fractions may be further purified by planet coil countercurrent chromatography (PCCC), using solvent systems consisting of hexane, methanol, methylene chloride, chloroform, toluene, and water or suitable aqueous buffers. The various fractions contain several taxane derivatives, including taxol, cephalomannine and baccatin III. The solvent is removed from the fraction containing compound 1, which is recrystallized from methanol or ethanol and water to afford the pure compound as white crystals. If desired, taxol, baccatin, and other related compounds may also be isolated from the various chromatographic fractions.

In general, the compounds of formula (II) may then be synthesized from compound 1 by a series of protection, reaction and deprotection steps. In one such process, illustrated below in Scheme 1, compound 1 is first protected at the 7- and 9-hydroxy groups by reaction with an aldehyde or a ketone, as for example acetone, in the presence of a small amount of acid to form a 1,3-dioxane such as an acetonide or similar protected intermediate (compound 2). This compound may next be deacetylated at the C-13 position, as for example by reaction with a base or by microbial hydrolysis, to give compound 3. Alternatively, compound 1 can be directly deacetylated prior to protection with reagents such as butyllithium, methyllithium or lithium triethylborohydride and the subsequent protection performed using various silyl groups such as triethylsilyl to protect either or both of the 7- and 9-hydroxyl groups.

Compound 3 may then be reacted with an appropriate protected side-chain derivative, for example (2R,3S)-N-benzoyl-O-(1-ethoxyethyl)-3-phenylisoserine or (3R,4S)-N-benzoyl-3-O-(1-ethoxyethyl)-4-phenyl-2-azetidinone, to produce compound 4 where R is the protected taxol side-chain or an analogous moiety. Selective deactylation of the C-10 acetate can be performed at this point using mild hydrolytic conditions to produce compounds having greater water solubility. The protecting groups may then be removed with a mild acid, as for example 0.5% HCl in ethanol or methanol, to produce the desired 9-dihydrotaxol of formula (II) in which $R^2$ and $R^5$ are acetyl, $R^3$, $R^4$ and $R^7$ are hydrogen, and $R^6$ is phenylcarbonyl.

Scheme 1

Alternative reaction schemes are shown below as Schemes 2, 3 and 4. According to Scheme 2, the deacetylation step is performed directly on compound 1 which can then be selectively protected at C-7 using various groups such as silylating reagents. Acylation and deprotection of compound 6 affords compound 9 which can, in turn, be deprotected to compound 10 as before. Alternatively deacetylation at the C-10 position and deprotection gives products such as compound 11 which are expected to have improved water solubility.

Compound 10 can also be directly reacted with aldehydes and ketones in the presence of acid as described in Scheme 1 to give compounds 12 (Scheme 3). Alternatively, reaction of compound 1 in a similar manner such as with 3-butenal produces compound 13 (W=H; Z=CH$_2$CH=CH$_2$) to which the lactam 7 of Scheme 1 can be added as before to produce compound 14. Oxidation and deprotection will afford compound 12c. By reacting compound 1 with carbonic, sulfuric, phosphoric or similar acid derivatives and base, products such as compound 13 (where W and Z together are sulfur) are produced.

Allylation at the C-7 position of compound 1 under standard conditions gives compound 15 (Scheme 4). Treatment with n-butyllythium as before and quenching with the lactam 7 gives compound 16 which can either be oxidized to compounds 19 and 20, or deprotected to compound 17. In addition, the aldehyde 20 can be reacted under reducing conditions with various amines followed by acid to give compound 21. Reduction with various reagents such as sodium borohydride produces compound 22, while acetylation of this reduction product followed by deprotection can give compound 23.

9
10

Scheme 2

Scheme 3

5,530,020

-continued
Scheme 3

Scheme 4

Particular reagents and conditions utilized in these syntheses are described in detail in the Examples which follow. Also, it will be appreciated by one skilled in the art that selective protection and deprotection steps affecting the several hydroxyl groups on the baccatin III structure may be carried out in varying order or number of steps, as necessary, and that Schemes 1–4 are intended to encompass such variations.

The foregoing may be better understood by reference to the following Examples, which are provided for purposes of illustration and not limitation of the invention.

EXAMPLE 1

Isolation and Characterization of 9-dihydro-13-acetylbaccatin III

A 30 g sample of an alcoholic extract of crushed needles and twigs of *Taxus canadensis* (obtained from Pelagic Laboratory, Inc., Port-Daniel, Quebec, Canada) was dissolved in 2 L of 9:1 methanol:water and extracted four times with 800 mL hexane. The aqueous phase was diluted with water (400 mL) and extracted four times with 800 mL carbon tetrachloride. The aqueous phase was further diluted with water (500 mL) and extracted four times with 800 mL methylene chloride, after which the pooled methylene chloride fractions were evaporated to a residue.

The methylene chloride soluble fraction (1.0 g) was separated on a PCCC using $CH_2Cl_2:CCl_4:MeOH:H_2O$ (5:5:10:6). The organic phase was used as the mobile phase and the fractions were monitored by thin layer chromatography (TLC). The fractions containing 9-dihydro-13-acetylbaccatin III from the first PCCC separation were combined and recrystallized from methanol/water to give 35 mg of the pure compound as white crystals (yield 0.37% of the extract). The structure of this compound was established by spectral analysis and confirmed by single crystal X-ray diffraction analysis.

Figure 1:
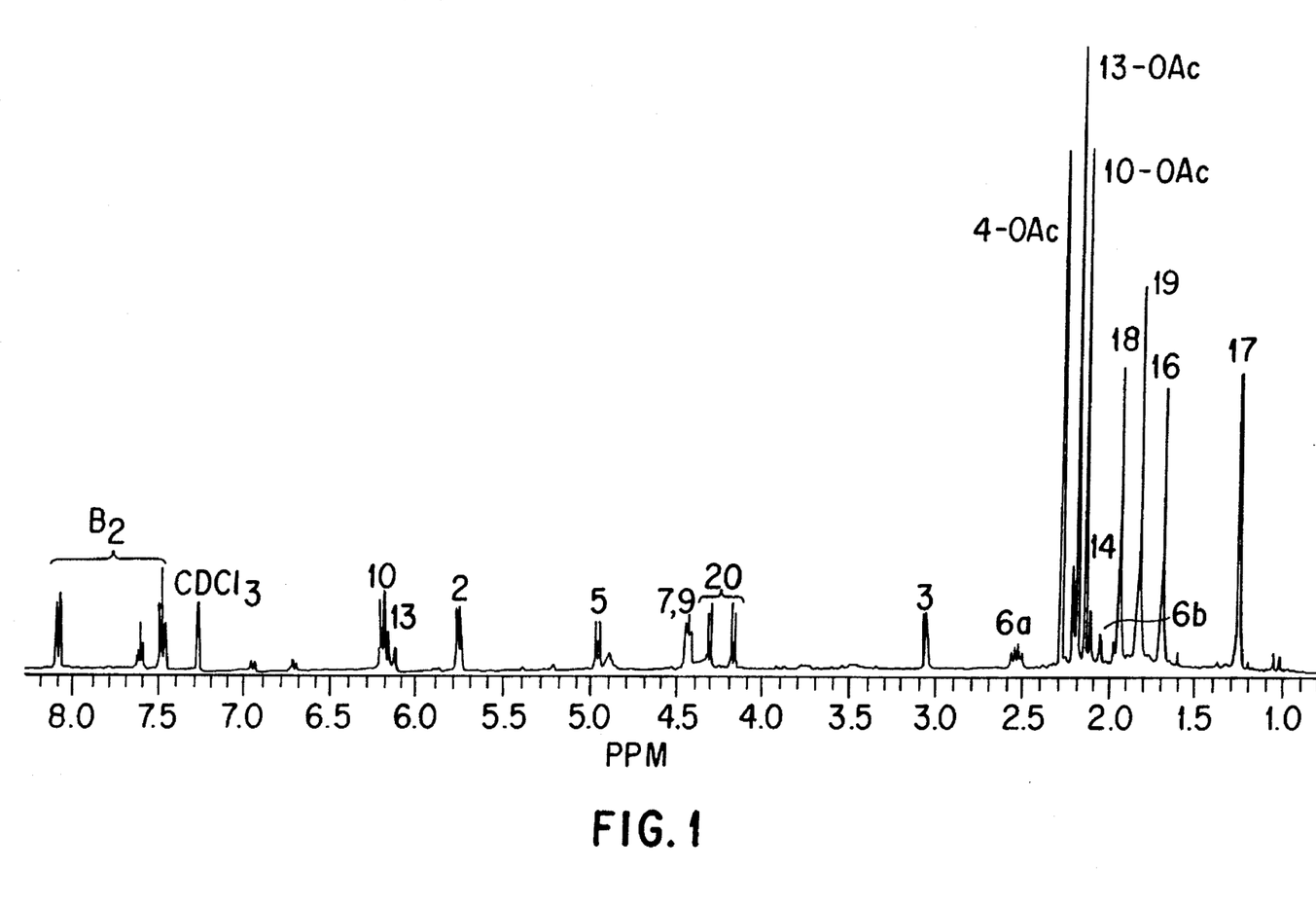
FIG. 1 is a hydrogen NMR Spectrum in $CDCl_3$ of 9-dihydro-13-acetylbaccatin III.

Physical data: Crystallized from methanol as clear rods; melting point, 221° C.; molecular weight (FABHRMS, MH+) calculated for $C_{33}H_{43}O_{12}$, 361.2754; observed, 361.2771; IR spectrum (KBr), 3500, 1725, 1720, 1375, 1220, 1060, 1010 $cm^{-1}$; NMR assignments, obtained by one- and two-dimensional proton and $^{13}C$ NMR, shown in FIG. 1 and Table 1, below.

Figure 2:
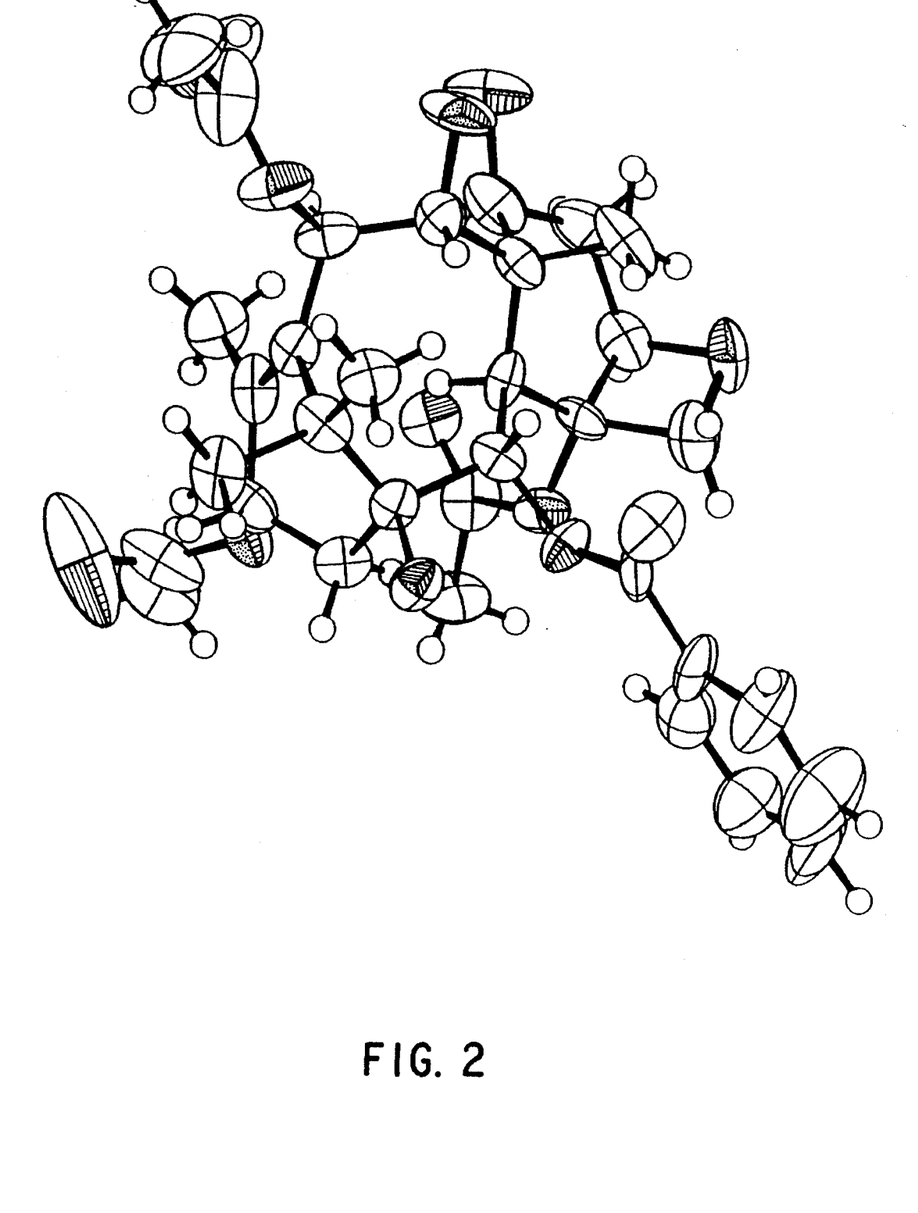
FIG. 2 is a depiction of the 3-dimensional structure of 9-dihydro-13-acetylbaccatin III.

Single crystal X-ray diffraction analysis: Source, Cu Kα; symmetry, monoclinic; unit cell constants, a=8.513 (3), b=16.164 (2), c=12.772 (2) Å, β=100.16 (2)° as determined from 25 diffractometer-measured 2θ values; systematic extinctions and density considerations uniquely consistent with space group $P2_1$ with one molecule of composition $C_{33}H_{42}O_{12}$ per symmetric unit; total reflections, 1605; solution obtained by direct methods, with structure illustrated in FIG. 2; in final model, non-hydrogen atoms anisotropic, hydrogen atoms isotropic, discrepancy index R=0.055.

TABLE 1

| NMR Spectral Data of 9-dihydro-13-acetylbaccatin III | | | |
|---|---|---|---|
| Position | 1H Shift (ppm from TMS) | multiplicity | 13C Shift (ppm from TMS) |
| C-1 | | | 79.51 |
| C-2 | 5.67 | (d) | 74.30 |
| C-3 | 3.05. | (d) | 49.83 |
| C-4 | 82.85 | | |
| C-5 | 4.95 | (d) | 84.83 |

TABLE 1-continued

| NMR Spectral Data of 9-dihydro-13-acetylbaccatin III | | | |
|---|---|---|---|
| Position | 1H Shift (ppm from TMS) | multiplicity | 13C Shift (ppm from TMS) |
| C-6 | 1.9 | (ddd) | 38.66 |
|  | 2.5 | (dd) |  |
| C-7 | 4.45 | (dd) | 74.65 |
| C-8 | 45.50 | | |
| C-9 | 4.45 | (d) | 77.51 |
| C-10 | 6.25 | (d) | 73.96 |
| C-11 | 135.74 | | |
| C-12 | 140.26 | | |
| C-13 | 6.25 | (dd) | 70.68 |
| C-14 | 2.2 (2H) | (m) | 36.10 |
| C-15 | 43.80 | | |
| C-16 | 1.67 | (s) | 23.34 |
| C-17 | 1.25 | (s) | 29.04 |
| C-18 | 1.92 | (s) | 15.59 |
| C-19 | 1.89 | (s) | 13.25 |
| C-20 | 4.19 | (d) | 77.32 |
|  | 4.30 | (d) | |
| C-2 OBz | | | |
| C=O | | | 167.75 |
| C-1' | | | 130.00 |
| C-2',6' | 8.1 | (d,) | 130.79 |
| C-3',4' | 7.46 | (dd) | 129.37 |
| C-4' | 7.62 | (dd) | 134.42 |
| C-4 OAc | | | |
| $CH_3$ | 2.3 | (s) | 23.57 |
| C=O | | | 170.13 |
| C-10 OAc | | | |
| $CH_3$ | 2.1 | (s) | 21.96 |
| C=O | | | 171.23 |
| C-13 OAc | | | |
| $CH_3$ | 2.2 | (s) | 22.07 |
| C=O | | | 171.37 |

EXAMPLE 2

9-Dihydrobaccatin III-7,9-acetonide

Step 1: 13-Acetyl-9-dihydrobaccatin III-7,9-acetonide

A 10 mg sample of 9-dihydro-13 acetyl-baccatin III from Example 1, above, was placed into a dry flask with 0.5 mL of acetone and 0.5 mL of 2,2-dimethoxypropane, and the solution stirred at 25° C. A crystal of camphorsulfonic acid was added, and the progress of the reaction followed by TLC. When TLC indicated that the reaction was complete, 25 mg of solid $NaHCO_3$ and 0.15 mL of saturated $NaHCO_3$ solution were added, and the mixture stirred for several minutes. Solid sodium sulfate was added, the mixture filtered and the solids rinsed with methylene chloride. Solvent was removed by evaporation and the resulting product chromatographed on silica gel, eluting with 3% methanol in methylene chloride, to afford 10 mg of the title compound as an oil. MS M/Z ($DCl/NH_3$): 671 (M+H+), 688 (M+NH3); $^1H$ NMR ($CDCl_3$) δ: 1.2 (s, 3H), 1.48 (s, 3H), 1.55 (s, 3H), 1.6 (s, 3H), 1.8 (s, 3H), 2.12 (br s, 3H), 2.15 (s, 3H), 2.2 (s, 3H), 2.3 (s, 3H), 2.51 (m, 1H), 3.15 (d, 1H), 4.22 (t, 1H), 4.25 (AB q, 2H), 4.53 (d, 1H), 4.91 (d, 1H), 5.87 (d, 1H), 6.14 (t, 1H), 6.5 (d, 1H), 7.5 (t, 2H), 7.62 (t, 1H), 8.1 (d, 2H).

Step 2: 9-Dihydrobaccatin III-7,9-acetonide

A 25 mg sample of the product of step 1 was dissolved in 1 mL of tetrahydrofuran and stirred under an inert atmosphere. A solution of n-butyl lithium in hexanes (90 µl, 1.6M) was added over ten minutes at −44° C. Saturated ammonium chloride solution (1 ml) was added and the solvents removed by evaporation. The product was chromatographed on silica gel, eluting with 5% methanol in methylene chloride to afford 11 mg of the title compound. $^1$HNMR (CDCl$_3$): partial δ 1.03 (s, 3H), 1.4 (s, 3H), 1.5 (s, 3H), 1.52 (s, 3H), 1.86 (s, 3H), 2.07 (s, 3H), 2.1 (d, 3H), 2.21 (s, 3H), 2.3–2.5 (m, 2H), 3.2 (d, 1H), 4.2 (ABq, 2H), 4.25 (t, 1H), 4.5 (d, 1H), 4.71 (m, 1H), 4.9 (d, 1H), 5.8 (d, 1H), 6.5 (d, 1H), 7.5 (t, 2H), 7.62 (t, 1H), 8.1 (d, 2H).

EXAMPLE 3

9-Dihydrotaxol

Step 1: 2'-Ethoxyethyl-9-dihydrotaxol-7,9-acetonide

A sample of the product of Example 2 is combined with 6 equivalents of optically pure (2R,2S)-N-benzoyl-O-(1-ethoxyethyl)-3-phenylisoserine [prepared as described by Denis et al., *J. Amer. Chem. Soc.* 110:5917 (1988), incorporated herein by reference], 6 equivalents of di-2-pyridyl carbonate, and 2 equivalents of 4-(dimethylamino)pyridine in toluene and heated at reflux for 100 hours or until TLC shows the reaction to be complete. The solvent is removed and the ester purified by chromatography on silica gel.

Alternatively, the product of Example 2 is reacted with (3R,4S)-N-benzoyl-3-O-(1-ethoxyethyl)-4-phenyl-2-azetidinone in the presence of base as described by Georg et al., *Bioorganic & Medicinal Chemistry Letters* 2(4):295 (1992) or Ojima et al., *J. Org. Chem.* 56:1681 (1991) [each incorporated herein by reference].

Step 2: 9-Dihydrotaxol

A sample of the product of step 1 is deprotected by reaction with an acid such as camphorsulfonic acid or 0.5% HCl in ethanol at 0° C. The resulting title compound is purified by chromatography on silica gel.

EXAMPLE 4

9-Dihydrobaccatin III

To 1 g of the product of Example 1 in THF at −78° C. were added 3–6 equivalents butyllithium or methyllithium dropwise until the deacetylation of the 13-acetate was complete as determined by thin layer chromatographic (TLC) analysis. The mixture was partitioned between buffer and methylene chloride, the organic layer dried with sodium sulfate, and evaporated. The crude product was purified (all purifications in this and the remaining Examples were performed by chromatography on silica gel either via flash column or preparative thin layer chromatography) using methanol/methylene chloride to give 0.7 g of 9-dihydrobaccatin III.

EXAMPLE 5

7-O-Triethylsilyl-9-dihydrobaccatin III

To 1.9 g of the product of Example 4 in 6 ml pyridine at 0° C. were added 1.5 equivalents of triethylsilyl chloride. After 16 hours the reaction was quenched, concentrated, and worked up as above. (In this an all other Examples, the buffer used to quench reactions was a pH 7 phosphate buffer.) After purification using ethyl acetate:hexane, 1.3 g of 7-O-triethylsilyl-9-dihydrobaccatin III was obtained.

EXAMPLE 6

2'-O-Ethoxyethyl-7-O-triethylsilyl-9-dihydrotaxol

To 0.24 g of the product of Example 5 in THF at −78° C. were added either 3 eq. of lithium hexamethyldisilazide (LiHMDS) or 5 to 40 eq. of sodium hydride. To this mixture were added 3 eq. of the lactam of Scheme 2 (compound 7, R=phenyl) and the reaction warmed to 0°–25° C. for 1–12 hours and quenched and purified using ethyl acetate:hexane to give 0.25 g of 2'-O-ethoxyethyl-7-O-triethylsilyl-9-dihydrotaxol.

EXAMPLE 7

2'-O-Ethoxyethyl-9-dihydrotaxol

To 0.25 g of the product of Example 6 in methanol at 0° C. was added an excess of hydrogen fluoride/pyridine solution containing equal amounts of triethylamine until reaction was complete as determined by TLC analysis. The mixture was quenched with buffer and purified using ethyl acetate:hexane to give 0.16 g of 2'-O-ethoxyethyl-9-dihydrotaxol.

EXAMPLE 8

9-Dihydrotaxol

To 60 mg of the product of Example 7 dissolved in ethanol at 0°–25° C. was added an excess of 1% HCl, and after four hours the reaction mixture was quenched with pH 7 buffer and methylene chloride. The organic layer was evaporated and purified using ethyl acetate:hexane to give 28 mg of 9-dihydrotaxol. The title compound was also obtained directly from the product of Example 6 by this treatment.

EXAMPLE 9

10-Deacetyl-9-dihydrotaxol

To 0.22 g of the product from Example 7 in methanol at 0° C. was added an excess of 1N KOH until reaction was complete as determined by TLC analysis. The reaction was quenched with buffer and methylene chloride. The organic layer was separated, evaporated, and treated directly with 1% HCl as in Example 8 to give (after purification using ethyl acetate:hexane) 0.164 g of 10-deacetyl-9-dihydrotaxol.

EXAMPLE 10

9-Dihydrotaxol-7,9-isopropylidene ketal

Treatment of 10 mg of the product of Step 1 of Example 3 with 1% HCl as in the previous Example gave, after purification with methanol/methylene chloride, 5 mg of 9-dihydrotaxol-7,9-isopropylidene ketal (Scheme 3, compound 12, X=Y=CH$_3$).

EXAMPLE 11

9-Dihydrotaxol-7,9-propylidene acetal

To 4 mg of the product of Example 8 in 0.5 ml of propionaldehyde was added a catalytic amount of p-toluenesulfonic acid (tosic acid) and the mixture stirred for four hours. The residue was partitioned between methylene chloride and aqueous sodium bicarbonate, and the organic layer was evaporated. Purification using ethyl acetate:hexane gave 2.6 mg of 9-dihydrotaxol-7,9-propylidene acetal (Scheme 3, compound 12, X=Y=CH$_2$CH$_3$).

EXAMPLE 12

9-Dihydrotaxol-7,9-benzylidene acetal 15 mg of the product of Example 8 were treated with 0.1 ml benzaldehyde in 0.6 ml methylene chloride to give 1.1 mg of 9-dihydrotaxol-7,9-benzylidene acetal (Scheme 3, compound 12, X=H, Y=Ph).

EXAMPLE 13

9-Dihydrotaxol-7,9-(3,4-dihydroxy)butylidene acetal

Step 1

To 0.25 g of the product of Example 1 in 5 ml methylene chloride were added 1 ml 3-butenal diethyl acetal and 2.3 mg tosic acid and stirred as above. The crude reaction mixture was purified using ethyl acetate:hexane to give 77 mg of 9-dihydro-13-acetylbaccatin III 7,9-(3,4-dihydroxy)butylidene acetal.

Step 2

To 39 mg of the product from Step 1 in 3 ml of tetrahydrofuran (THF) at −78° C. was added 5.3 eq. butyllithium dropwise and the mixture warmed to −44° C. To this was added 1.9 eq. of the lactam of Scheme 2 (compound 7, R=phenyl) and the mixture rewarmed to 0° C. for 1 hour and quenched with buffer. The reaction mixture was partitioned between ethyl acetate and water the organic layer was dried, evaporated and purified using ethyl acetate:hexane to give 11.3 mg of 2'O-ethoxyethyl-9-dihydrobaccatin III 7,9-(3,4-dihydroxy)butylidene acetal as a mixture of diastereomers.

Step 3

To 5.3 mg of the product of Step 2 in 0.8 ml THF:water (5:1) were added 2 eq. N-methylmorpholine N-oxide and a catalytic amount of osmium tetraoxide. The reaction mixture was stirred for 2 hours and quenched by the addition of excess sodium thiosulfate and CELITE filter agent, filtered, rinsed with ethanol/methylene chloride, and evaporated. The residue was dissolved in ethanol and treated with excess 1% HCl for 4 hours, quenched with buffer, and purified using methanol/methylene chloride to give 1 mg of 9-dihydrotaxol-7,9-(3,4-dihydroxy)butylidene acetal.

EXAMPLE 14

9-Dihydrotaxol-7,9-thionocarbonate

Step 1

To 50 mg of the product of Example 1 in toluene was added 3 eq. thiocarbonyldiimidazole and a catalytic amount of dimethylaminopyridine (DMAP). The mixture was heated to reflux for 1 hour, washed with pH 7 buffer, and worked up as above. After purification using methanol:methylene chloride there was obtained 49.5 mg of 9-dihydrobaccatin III-7,9-thionocarbonate.

Step 2

47 mg of the product of Step 1 were treated with butyllithium and the lactam reagent of Scheme 2 (compound 7, R=phenyl) and HCl as in Example 8 above to give, after purification with methanol:methylene chloride, 12 mg of 9-dihydrotaxol-7,9-thionocarbonate.

EXAMPLE 15

9-Dihydrotaxol-7-O-allyl ether

Step 1

To 0.19 mg of the product of Example 1 in THF at 0° C. were added 9 eq. of sodium hydride, a catalytic amount of tetrabutylammonium iodide, and 1.1 eq. of allyl bromide. After 12 hours the reaction was quenched with buffer and ethyl acetate. The organic layer was dried and evaporated, and the crude residue purified using ethyl acetate:hexane to give 61 mg of 9-dihydrobaccatin II 7-O-allyl ether.

Step 2

To 61 mg of the product of Step 1 in THF at −78° C. were added 6 eq. of butyllithium dropwise and 2 eq. of the lactam reagent of Scheme 2 (compound 7, R =phenyl) were added. The mixture was warmed to 0° C. for 1 hour and quenched as above. After purification using ethyl acetate:hexane, there were obtained 25 mg of crude product. This material was treated with 1% HCl as in Example 8 to produce 9-dihydrotaxol-7-O-allyl ether.

EXAMPLE 16

9-Dihydrotaxol 7-O-(2,3-Dihydroxypropyl) ether

To 4 mg of the product of Example 15, Step 2, in THF:water (5:1) were added 2 eq. N-methylmorpholine N-oxide and a catalytic amount of osmium tetraoxide. After 2 hours the mixture was quenched by the addition of excess sodium thiosulfate and CELITE filter agent, filtered, and evaporated to give crude material. Direct treatment of this material with 1% HCl as above afforded 3.5 mg of 9-dihydrotaxol 7-O-(2,3-dihydroxypropyl) ether.

EXAMPLE 17

9-Dihydrotaxol 7-O-(2-Dimethylaminoethyl) ether

Step 1

Into 27 mg of the crude product of Example 15, Step 2, in methanol:methylene chloride at −78° C. was bubbled excess ozone until disappearance of starting material took place. The reaction was purged with nitrogen and quenched by addition of an excess of dimethyl sulfide at 25° C. The crude product was purified as above using ethyl acetate:hexane to give 22 mg of 9-dihydrotaxol-7-O-(2-methylenecarboxaldehyde).

Step 2

To 8 mg of the product of Step 1 above in ethanol were added 10 eq. diethylamine and 10 eq. of acetic acid, followed by excess sodium cyanoborohydride. After two hours, the reaction was directly treated with 1% HCl as above to give 5.4 mg of 9-dihydrotaxol 7-O-(2-dimethylaminoethyl) ether.

EXAMPLE 18

9-Dihydrotaxol 7-O-(2-Hydroxyethyl) ether

To 5 mg of the product of Example 17, Step 1, in methanol was added an excess of sodium borohydride and, after 1 hour, the reaction quenched with pH 7 buffer as above. The crude residue was directly treated with 1% HCl as above to afford (after purification using 5% methanol in methylene chloride) 2.2 mg of 9-dihydrotaxol 7-O-(2-hydroxyethyl) ether.

EXAMPLE 19

9-Dihydrotaxol 7-O-(2-Acetoxyethyl) ether

The product of Example 18 was also directly acetylated by treatment with excess acetic anhydride in pyridine for 3 hours. Following evaporation of the solvents the crude product was treated with 1% HCl as in Example 8 and purified using methanol/methylene chloride to give 9-dihydrotaxol 7-O-(2-acetoxyethyl) ether.

EXAMPLE 20

N-Debenzoyl-N-t-butoxycarbonyl-9-dihydrotaxol

Step 1

0.1 g of the product of Example 5 was treated with either 3 eq. of lithium hexamethyldisilazide (LiHMDS) or 5–40 eq. of sodium hydride as in Example 6 and 0.132 g of the lactam reagent of Scheme 2 (compound 7, R=tert-butoxy) to give (after purification using acetone:hexane) 0.144 g of 7-O-triethylsilyl-2'-O-ethoxyethyl-N-debenzoyl-N-t-butoxycarbonyl-9-dihydrotaxol.

Step 2

Treatment of 4 mg of the product of Step 1 with HF/pyridine/triethylamine as in Example 7, followed by direct treatment with HCl, gave, after purification using methanol/methylene chloride, 1.5 mg of N-debenzoyl-N-t-butoxycarbonyl-9-dihydrotaxol.

EXAMPLE 21

10-Deacetyl-N-debenzoyl-N-t-butoxycarbonyl-9-dihydrotaxol

Treatment of 0.275 g of the product of Example 20, Step 1, as above with HF/pyridine/triethylamine followed by treatment of the desilylated product with KOH as in Example 9 and 1% HCl as in Example 8 gave 93.3 mg 10-deacetyl-N-debenzoyl-N-t-butoxycarbonyl-9-dihydrotaxol.

EXAMPLE 22

N-Debenzoyl-N-t-butylacetyl-9-dihydrotaxol

Step 1

10 mg of the product of Example 5 were treated as in Example 20, Step 1, with 16 mg of the lactam reagent of Scheme 2 (compound 7, R=tert-butyl-CH$_2$) to give (after purification using acetone:hexane) 10 mg of 7-O-triethylsilyl-2'-O-ethoxyethyl-N-debenzoyl-N-t-butylacetyl-9-dihydrotaxol.

Step 2

10 mg of the product from Step 1 were deprotected as in Example 20, Step 2, by treatment with HF/pyridine/triethylamine and HCl to give 2.2 mg of N-debenzoyl-t-butylacetyl-9-dihydrotaxol.

EXAMPLE 23

N-Debenzoyl-N-isobutoxycarbonyl-9-dihydrotaxol

Step 1

20 mg of the product of Example 5 were treated as above with 29 mg of lactam reagent (R=iso-butoxy) to give (after purification using ethyl acetate:hexane) 19.3 mg of 7-O-triethylsilyl-2'-O-ethoxyethyl-N-debenzoyl-N-isobutoxycarbonyl-9-dihydrotaxol.

Step 2

19 mg of the product of Step 1 above were deprotected as before by treatment with HF/pyridine/triethylamine and HCl to give 9.2 mg of N-debenzoyl-N-isobutoxycarbonyl-9-dihydrotaxol.

EXAMPLE 24

N-Debenzoyl-N-adamantoxycarbonyl-9-dihydrotaxol

Step 1

15 mg of the product of Example 5 were treated as above with 26 mg of lactam reagent (R=adamantoxy) to give (after purification using ethyl acetate:hexane) 20.8 mg of 7-O-triethylsilyl-2'-O-ethoxyethyl-N-debenzoyl-N-adamantoxycarbonyl-9-dihydrotaxol.

Step 2

20 mg of the product of Step 1 above were deprotected as before by treatment with HF/pyridine/triethylamine and HCl to give 11 mg of N-debenzoyl-N-adamantoxycarbonyl-9-dihydrotaxol.

EXAMPLE 25

N-Debenzoyl-N-isopropoxycarbonyl-9-dihydrotaxol

Step 1

15 mg of the product of Example 5 were treated as above with 21 mg of lactam reagent (R=2-propoxy) to give (after purification using ethyl acetate:hexane) 14.1 mg of 7-O-triethylsilyl-2'-O-ethoxyethyl-N-debenzoyl-N-isopropoxycarbonyl-9-dihydrotaxol.

Step 2

14 mg of the product of Step 1 above were deprotected as before by treatment with HF/pyridine/triethylamine and HCl to give 9.1 mg of N-debenzoyl-N-isopropoxycarbonyl-9-dihydrotaxol.

EXAMPLE 26

N-Debenzoyl-N-benzyloxycarbonyl-9-dihydrotaxol

Step 1

84 mg of the product of Example 5 were treated as above with 160 mg of lactam reagent (R=2-benzyloxy) to give (after purification using ethyl acetate:hexane) 76 mg of 7-O-triethylsilyl-2'-O-ethoxyethyl-N-debenzoyl-N-benzyloxycarbonyl-9-dihydrotaxol.

Step 2

76 mg of the product from Step 1 above is deprotected as before by treatment with HCl to give 32 mg of N-debenzoyl-N-benzyloxycarbonyl-9-dihydrotaxol.

EXAMPLE 27

N-Debenzoyl-9-dihydrotaxol

To 32 mg of the product of Example 26 in 2-propanol were added 16 mg 10% Pd/C and the mixture stirred under hydrogen for two days. The reaction was filtered and the solvent evaporated to give 27 mg of crude amine, N-debenzoyl 9-dihydrotaxol.

EXAMPLE 28

N-Debenzoyl-N-pivaloyl-9-dihydrotaxol

To 6 mg of the product of Example 27 in 0.5 ml methylene chloride were added an excess of triethylamine and 5 eq. of pivaloyl chloride. This mixture was quenched with methanol and purified using methanol/methylene chloride to give 2.2 mg of N-debenzoyl-N-pivaloyl-9-dihydrotaxol.

EXAMPLE 29

N-Debenzoyl-N-acetyl-9-dihydrotaxol

In a manner similar to that of the previous Example, acetic anhydride was reacted with 7 mg of the product of Example 27 without base to give (after purification using methanol/methylene chloride) 3 mg of N-debenzoyl-N-acetyl-9-dihydrotaxol.

EXAMPLE 30

N-Debenzoyl-N-t-butylcarbamyl-9-dihydrotaxol

In a manner similar to that of the previous Examples, tert-butylisocyanate and a catalytic amount of 4-dimethylaminopyridine were reacted with 6 mg of the product of Example 27 to give (after purification using methanol/methylene chloride) 2.9 mg of N-debenzoyl-N-t-butylcarbamyl-9-dihydrotaxol.

EXAMPLE 31

Physical Characterization of Compounds of the Invention

Proton NMR and mass spectrographic characterization of the compounds of the present invention yielded the data shown below in Table 2.

TABLE 2

Physical Characteristics of the Compounds

| Ex. | $^1$H NMR δ (ppm) | | | | MS |
|---|---|---|---|---|---|
| | H-10 | H-3' | H-9 | H-7 | |
| 8 | 6.19 | 5.69 | 4.5 | 4.37 | 856(M+H)$^+$ |
| 9 | 4.83 | 5.79 | 4.25 | 4.24 | 796(M+Na)$^+$ |
| 10 | 6.42 | 5.62 | 4.53 | 4.18 | 896(M+H)$^+$ |
| 11 | 6.78 | 5.64 | 4.5 | 3.99 | 896(M+H)$^+$ |
| 12 | 6.65 | 5.64 | 4.65 | 4.17 | 944(M+H)$^+$ |
| 13 | 6.15 | 5.63 | 5.47 | 4.57 | 980(M+K)$^+$ |
| 14* | 6.32 | 5.63 | 5.28 | 4.8 | 936(M+K)$^+$ |
| 15 | 6.28 | 5.67 | 4.54 | 4.25 | 934(M+K)$^+$ |
| 16 | 6.20 | 5.68 | 4.45 | 4.22 | 968(M+K)$^+$ |
| 17 | 6.18 | 5.67 | 4.42 | 4.20 | 955(M+H)$^+$ |
| 18 | 6.22 | 5.68 | 4.58 | 4.21 | 938(M+K)$^+$ |
| 19 | 6.24 | 5.67 | 4.59 | 4.21 | 980(M+K)$^+$ |
| 20* | 6.13 | 5.61 | 4.45 | 4.35 | 890(M+K)$^+$ |
| 21* | 4.9 | 5.65 | 4.31 | 4.29 | 848(M+K)$^+$ |
| 22* | 6.12 | 5.63 | 4.45 | 4.35 | 888(M+K)$^+$ |
| 23* | 6.12 | 5.83 | 4.43 | 4.38 | 890(M+K)$^+$ |
| 24* | 6.15 | 5.6 | 4.43 | 4.38 | 968(M+K)$^+$ |
| 25* | 6.13 | 5.74 | 4.43 | 4.36 | 838(M+H)$^+$ |
| 26* | 6.13 | 5.96 | 4.42 | 4.33 | 886(M+H)$^+$ |
| 28* | 6.11 | 5.59 | 4.43 | 4.34 | 874(M+K)$^+$ |
| 29* | 6.12 | 5.65 | 4.45 | 4.35 | — |
| 30* | 6.16 | 5.37 | 4.45 | 4.37 | 889(M+K)$^+$ |

For the products of Example numbers marked with an asterisk (*), NMR samples were tested in CDCl$_3$; all other samples were tested in MeOH.

EXAMPLE 32

Assay for In Vitro Tumor Cell Cytotoxicity

The compounds of the present invention were tested for in vitro cytotoxic activity against the tumor lines A549 (human breast cancer) and P-388 (mouse leukemia. IC$_{50}$'s were measured in a colorimetric assay for cytotoxic activity against cultured cells according to the protocol described below:

A three day microtiter assay was used to measure the growth inhibition of cultured cells exposed to a range of drug concentrations. Metabolic activity was measured by the cells' ability to reduce the tetrazolium dye, MTT (3-(4,5-dimethyl-thiazol-2-yl-2,5-diphenyltetrazolium bromide) to a quantifiable colored end product, which absorbs at 570 nm in the visible spectrum. Surviving cells reduce the MTT dye.

Test compounds were dissolved in dimethyl sulfoxide (DMSO) and diluted, first with Earle's Balanced Salt Solution, followed by culture medium, to twice the highest concentration of compound to be tested. From this concentrated stock, two-fold serial dilutions were prepared in 96-well microtiter trays, each well containing twice the desired final concentration of compound. Each concentration was tested in triplicate and compared to triplicate drug-free controls.

The cells were grown in the same medium used for diluting the compounds and then harvested using trypsinization. This involved removing the medium by aspiration;

rinsing the cell monolayer twice with Earle's Balanced Salt Solution; adding trypsin (0.05%)/EDTA (0.53 mM; for each 25 $cm^2$, approximately 0.2 mL), tilting to cover the monolayer, and then withdrawing trypsin leaving only a thin film of solution; incubating at room temperature until the cell monolayers detached (as determined by visual and/or microscopic observation); adding medium containing fetal calf serum to stop the action of the trypsin and resuspend the cells; triturating to aid dissociation of cell clumps; and determining the number of cells per milliliter by electronic cell counter (e.g. Coulter Counter) or by mixing an aliquot of cell suspension with Trypan Blue (0.4% in normal saline) and counting the viable cells using a hemacytometer.

After harvesting and determination of viable cell counts, cell density was adjusted to 25,000 cells/mL. Inoculum (0.1 mL) containing the cells was then added to each well for a final concentration of 2,500 cells per well. Addition of the inoculum diluted the test compounds to the desired final concentration.

Microtiter trays were then incubated for three days at 36° C. in a humidified atmosphere containing 5% carbon dioxide. After three days, 20 microtiters of 5 mg/mL MTT in phosphate-buffered saline solution were added to each well. Trays were returned to the incubator for two to four hours to allow the surviving cells to reduce the dye. Medium and unreduced dye were removed by aspiration. DMSO was added to each well to dissolve the water-insoluble, colored end product of the dye reduction so that it could be measured spectrophotometrically at 570 nm. The $IC_{50}$ was determined as the concentration of compound tested required to reduce the absorbance at 570 nm to 50% of non-drug treated control values.

The results of testing, shown in Table 3, below, demonstrate the cytotoxic activity of the compounds of the present invention.

TABLE 3

| In vitro tumor cell cytotoxicity ($IC_{50}$ μg/mL) | | |
|---|---|---|
| Example No. | A549 | P-388 |
| 8 | 0.016 | 0.049 |
| 9 | 0.011 | 0.14 |
| 10 | 0.025 | 0.042 |
| 11 | 0.023 | 0.022 |
| 12 | 1.0 | 1.0 |
| 13 | 0.3 | 0.18 |
| 14 | 0.019 | 0.035 |
| 15 | 0.001 | 0.0053 |
| 16 | 0.626 | >1.0 |
| 17 | 0.4 | 0.31 |
| 18 | 0.039 | 0.17 |
| 19 | 0.12 | 0.079 |
| 20 | 0.0003 | 0.0025 |
| 21 | 0.00026 | 0.0028 |
| 22 | 0.027 | 0.052 |
| 23 | 0.0043 | 0.028 |
| 24 | 0.0043 | 0.01 |
| 25 | 0.0012 | 0.0092 |
| 26 | 0.031 | 0.057 |
| 28 | 0.11 | 0.083 |
| 29 | 2.1 | 2.02 |
| 30 | 0.014 | 0.017 |

It is understood that the foregoing detailed description and accompanying examples are merely illustrative and are not to be taken as limitations upon the scope of the invention, which is defined solely by the appended claims and their equivalents. Various changes and modifications to the disclosed embodiments, which will be apparent to those skilled in the art, may be made without departing from the spirit and scope of the present invention.

What is claimed:

1. A compound having the formula wherein $R^1$ is a group having the formula in which $R^8$ is selected from the group consisting of hydrogen, phenyl, substituted phenyl, alkoxy, substituted alkoxy, amino, substituted amino, phenoxy and substituted phenoxy; $R^9$ is selected from the group consisting of hydrogen, alkyl, hydroxyalkyl, alkoxyalkyl, aminoalkyl, phenyl and substituted phenyl; and $R^{10}$ is selected from the group consisting of hydrogen, alkanoyl, substituted alkanoyl and aminoalkanoyl;

$R^2$, $R^5$ and $R^7$ are independently selected from the group consisting of hydrogen, alkyl, alkanoyl and aminoalkanoyl;

$R^4$ is hydrogen;

$R^3$ is selected from the group consisting of hydrogen, alkyl and aminoalkanoyl; and

$R^6$ is selected from the group consisting of hydrogen, alkyl, alkanoyl, aminoalkanoyl and phenylcarbonyl.

2. A compound according to claim 1 wherein $R^1$ is a group having the formula

3. A compound according to claim 1 wherein $R^3$ is hydrogen.

4. A compound having the formula wherein $R^1$ is a group having the formula in which $R^8$ is selected from the group consisting of hydrogen, phenyl, substituted phenyl, alkoxy, substituted alkoxy, amino, substituted amino, phenoxy and substituted phenoxy; $R^9$ is selected from the group consisting of hydrogen, alkyl, hydroxyalkyl, alkoxyalkyl, aminoalkyl, phenyl and substituted phenyl; and $R^{10}$ is selected from the group consisting of hydrogen, alkanoyl, substituted alkanoyl and aminoalkanoyl;

$R^2$, $R^5$ and $R^7$ are independently selected from the group consisting of hydrogen, alkyl, alkanoyl and aminoalkanoyl;

$R^4$ is hydrogen;

$R^6$ is selected from the group consisting of hydrogen, alkyl, alkanoyl, aminoalkanoyl and phenylcarbonyl; and $R^3$, taken together with one of $R^2$ and $R^4$, may form a ring having the formula in which $R^{11}$ and $R^{12}$ are chosen such that (i) each is independently selected from the group consisting of hydrogen, alkyl, phenyl and substituted phenyl; (ii) taken together, $R^{11}$ and $R^{12}$ are a single atom selected from the group consisting of oxygen and sulfur; or (iii) one of $R^{11}$ and $R^{12}$ is selected from the group consisting of hydrogen, alkyl, phenyl and substituted phenyl, and the other is —$OR^{13}$ or —$NR13R^{14}$ where $R^{13}$ and $R^{14}$ are independently selected from the group consisting of alkyl, alkanoyl, substituted alkanoyl, phenyl and substituted phenyl.

5. A compound according to claim 4 wherein $R^4$ is a group having the formula

* * * * *

UNITED STATES PATENT AND TRADEMARK OFFICE
CERTIFICATE OF CORRECTION

PATENT NO. : 5,530,020
DATED : June 25, 1996
INVENTOR(S) : G. P. Gunawardana, L. L. Klein, and J. B. McAlpine It is certified that error appears in the above-indentified patent and that said Letters Patent is hereby corrected as shown below:

In column 28, line 17, change "$R^4$" to read --$R^1$--.

Signed and Sealed this

Eighth Day of October, 1996

Attest:

BRUCE LEHMAN

Attesting Officer        Commissioner of Patents and Trademarks